(12) United States Patent
Qvist et al.

(10) Patent No.: US 6,867,188 B2
(45) Date of Patent: Mar. 15, 2005

(54) USE OF A BIOADHESIVE COMPOSITION COMPRISING A POLYPHENOLIC PROTEIN

(75) Inventors: Magnus Qvist, Alingsas (SE); Hans Arne Hansson, Hovas (SE)

(73) Assignee: BioPolymer Products of Sweden AB, Alingsas (SE)

(*) Notice: Subject to any disclaimer, the term of this patent is extended or adjusted under 35 U.S.C. 154(b) by 0 days.

(21) Appl. No.: 10/168,093

(22) PCT Filed: Dec. 14, 2000

(86) PCT No.: PCT/SE00/02533

§ 371 (c)(1),
(2), (4) Date: Oct. 15, 2002

(87) PCT Pub. No.: WO01/44401

PCT Pub. Date: Jun. 21, 2001

(65) Prior Publication Data

US 2003/0065060 A1 Apr. 3, 2003

Related U.S. Application Data

(60) Provisional application No. 60/178,548, filed on Jan. 26, 2000.

(30) Foreign Application Priority Data

Dec. 17, 1999 (SE) ................................. 9904650
Mar. 10, 2000 (SE) ................................. 0000799

(51) Int. Cl.$^7$ ............................ A01N 1/00; A61K 38/00
(52) U.S. Cl. ............................ 514/12; 524/17; 524/25; 524/21; 523/112; 523/118
(58) Field of Search ............................ 514/12; 524/21, 524/17, 25, 22; 523/112, 118; 530/350, 328; 424/19, 21, 17, 22, 32, 78, 81; 350/106; 623/13

(56) References Cited

U.S. PATENT DOCUMENTS

| 5,015,677 A | | 5/1991 | Benedict et al. |
| 5,030,230 A | | 7/1991 | White |
| 5,078,744 A | * | 1/1992 | Chvapil .................. 606/86 |

FOREIGN PATENT DOCUMENTS

| WO | 88/03953 | 6/1988 |
| WO | 94/28937 | 12/1994 |

OTHER PUBLICATIONS

C. Benedict et al. Chapter 33, "Adhesives from Marine Mussels", ACS Symp. Ser. (1989), 385 (Adhes. Renewable Resour.) pp. 465–483.
J. Waite et al., "Polyphenolic Substance of *Mytilus edulis*: Novel Adhesive Containing L–Dopa and Hydroxyproline", SCIENCE, vol. 212, May 1981, pp. 1038–1040.
T. Deming, "Mussel byssus and biomolecular materials", Current Opinion in Chemical Biology, vol. 3., 1999, pp. 100–105.
M. Yu et al., "Synthetic Polypeptide Mimics of Marine Adhesives", Macromolecules, vol. 31, 1998, pp. 4739–4745.
J. Waite, "Mussel glue from *Mytilus californianus* Conrad: a comparative study", J. Comp Physiol B., vol. 156, 1986, pp. 491–496.
R. Strausberg et al., "Protein–based medical adhesives", TIBTECH, vol. 8, 1990, pp. 53–57.
Jeffrey B. Robin et al., "Preliminary Evaluation of the Use of Mussel Adhesive Protein in Experimental Epikeratoplasty," Arch Ophthalmol, V. 106, 1988, pp. 973–977.

* cited by examiner

Primary Examiner—Robert A. Wax
Assistant Examiner—Robert B. Mondesi
(74) Attorney, Agent, or Firm—Young & Thompson

(57) ABSTRACT

A non-irritating, non-allergenic and non-toxic bioadhesive composition can be obtained by providing a bioadhesive composition including a polyphenolic protein derived from byssus-forming mussels and, b) a polymer comprising carbohydrate groups. The bioadhesive composition does not contain any enzyme or chemical cross-linking agent. Optionally, the composition may contain an oxidising agent and/or a filler protein. Preferably, the composition is provided as a kit of at least two parts, namely the polyphenolic protein and the polymer comprising carbohydrate groups, respectively. The composition is especially suitable as an adhesive in ophthalmic therapy.

6 Claims, No Drawings

USE OF A BIOADHESIVE COMPOSITION COMPRISING A POLYPHENOLIC PROTEIN

CROSS REFERENCE TO RELATED APPLICATION

This application is a national stage application of International Application PCT/SE00/02533, filed on Dec. 14, 2000 designating the United States of America.

The present invention relates to biodegradable compositions comprising adhesive, biocompatible polymers and methods used to cover surfaces and to attach structures to eye tissues, such as the cornea. Polyphenolic proteins isolated from mussels, referred to as "mussel adhesive protein" or "MAP", are used in conjunction with polysaccharides to achieve strong adhesive bonding. The invention also relates to a kit consisting of a MAP preparation, a preparation of polysaccharides which preferably are negatively charged, and optionally an oxidising agent such as hydrogen peroxide nitroprusside ions or periodate ions, that is used for preparing a composition for covering and attaching structures to eye tissue, such as cornea.

BACKGROUND OF THE INVENTION

The repair of traumatised structures on and in an eye and its adnexa is often troublesome. The use of sutures in e.g. the cornea is causing discomfort, deformations, distortions and may impair the visual acuity. Other eye components, such as the iris, lens structures and the retina are difficult or hardly possible to suture or to join with clips and related aids. Furthermore, sutures and clips do inevitably induce foreign body reactions and scar formation. The positioning of an implant in ocular structures, e.g. a partial-thickness or a penetrating keratoplasty or a prosthesis in the cornea, requires the use of elaborated techniques including the use of haptics to keep it retained in proper position, which may lead to irritations and adverse reactions. Accordingly, current methods for repairing structures on, at, and in an eye are associated with discomfort and the possibility of inducing permanent damage to the visual acuity. The use of a composition enabling structures with wet surfaces to be attached in desired position, remaining adherent for a predicted time period without causing any opacities in optically important components, or any deformation, scars or unacceptable foreign body reactions would therefore be highly desirable.

Polyphenolic proteins, preferentially isolated from mussels, are known to act as adhesives. Examples of such proteins can be found in e.g. U.S. Pat. No. 4,585,585. Their wide use as adhesives has been hampered by problems related to the purification and characterisation of the adhesive proteins in sufficient amounts. Furthermore, the requirement for biocompatible suitable cross-linkers and other additives have limited their use. Chemicals, such as bifunctional conjugating compounds, and enzymes are commonly associated with toxic reactions and other biomedical side effects. Additionally, it is difficult to extensively purify enzymes with retained high activity, avoiding denaturation and adverse effects on cells, tissues or organs.

Mussel adhesive protein (MAP) is formed in a gland in the foot of byssus-forming mussels, such as the common blue mussel (*Mytilus edulis*). The molecular weight of MAP from *Mytilis edulis* is about 130.000 Dalton and it has been disclosed to consist of 75–80 closely related repeated peptide sequences. The protein is further characterised by its many epidermal growth factor like repeats. It has an unusual high proportion of hydroxy-containing amino acids such as hydroxyproline, serine, threonine, tyrosin, and the uncommon amino acid 3,4 dihydroxy-L-phenylalanine (Dopa) as well as lysine. It may be isolated either from natural sources or produced biotechnologically. U.S. Pat. No. 5,015,677 as well as U.S. Pat. No. 4,585,585 disclose that MAP has very strong adhesive properties after oxidation and polymerisation, e.g. by the activity of the enzyme tyrosinase, or after treatment with bifunctional reagents. It is very important in biomedical applications of an adhesive and coating composition to use bioacceptable and biodegradable components, which furthermore should not per se or due to contamination induce any inflammation or toxic reactions. Fillers, including collagens and polysaccharides, have been added to improve the mechanical properties in cases when MAP was used to bond tissues and structures together, further adding to the risk for immunological reactions.

It is also previously known that it is possible to use adhesive compositions based on MAP for ophthalmic purposes. Robin et al., Refractive and Corneal Surgery, vol. 5, p. 302–306, and Robin et al., Arch. Ophthalmol., vol. 106, p. 973–977, both disclose MAP-based adhesives comprising an enzyme polymiser. U.S. Pat. No. 5,015,677 also describes a MAP-based adhesive containing a cross-linking agent and optionally a filler substance and a surfactant. Preferred cross-linking agents according to U.S. Pat. No. 5,015,677 are enzymatic oxidising agents such as catechol oxidase and tyrosinase, but sometimes also chemical cross-linking agents such as glutaraldehyde and formaldehyde. Examples of fillers are proteins, such as collagen and albumin, and polymers comprising carbohydrate moieties, such as chitosan and hyaluronan. U.S. Pat. No. 5,030,230 also relates to a bioadhesive comprising MAP, mushroom tyrosinase (cross-linker), SDS (sodium dodecyl sulfate, a surfactant) and collagen (filler). The bioadhesive is used to adhere a cornea prosthesis to the eye wall.

A major problem associated with known MAP-based bioadhesive compositions, despite the superior properties of MAP per se, is that some constituents, in particular the presently used cross-linking agents, can harm and/or irritate living tissue and cause toxic and immunological reactions. Chemical crosslinking agents, such as glutaraldehyde and formaldehyde, are generally toxic to humans and animals, and it is highly inappropriate to add such agents to a sensitive tissue, such as the eye. Enzymes, such as catechol oxidase and tyrosinase, are proteins, and proteins are generally recognised as potent allergens, especially in case they originate from a species other than the patient. Because of their oxidising and hydrolysing abilities, they can also harm sensitive tissue. Despite these serious drawbacks associated with the presently used cross-linkers, it has been regarded as necessary to include them in order to obtain sufficient curing of the bioadhesive.

Accordingly, there is a need for a MAP-based bioadhesive composition which overcomes these drawbacks and hence, does not harm or irritate sensitive tissues such as the eye.

SUMMARY OF THE INVENTION

Now it has surprisingly been found that a non-irritating, non-allergenic and non-toxic composition can be obtained by providing a bioadhesive composition comprising a) a polyphenolic protein derived from byssus-forming mussels b) a polymer comprising carbohydrate groups. The bioadhesive composition does not contain any enzyme or chemical cross-linking agent. Optionally, the composition may contain an oxidising agent and/or a filler protein. Preferably, the composition is provided as a kit of at least two parts, namely the polyphenolic protein and the polymer comprising carbohydrate groups, respectively.

Definitions

As disclosed herein, the terms "polyphenolic protein", "mussel adhesive protein" or "MAP" relates to a bioadhesive protein derived from byssus-forming mussels. Examples of such mussels are mussels of the genera *Mytilus, Geukensia, Aulacomya, Phragmatopoma, Dreissenia* and *Brachiodontes*. Suitable proteins have been disclosed in a plurality of publications, e.g. U.S. Pat. Nos. 5,015,677, 5,242,808, 4,585,585, 5,202,236, 5,149,657, 5,410,023, WO 97/34016, and U.S. Pat. No. 5,574,134, Vreeland et al., J. Physiol., 34: 1–8, and Yu et al., Macromolecules, 31: 4739–4745. They comprise about 30–300 amino acid residues and essentially consist of tandemly linked peptide units optionally separated by a junction sequence of 0–10 amino acids. A characteristic feature of such proteins is a comparatively high amount of positively charged lysine residues, and in particular the unusual amino acid DOPA (L-3,4-dihydroxyphenylalanine). A polyphenolic protein suitable for use in the present invention has an amino acid sequence in which at least 5% and preferably 6–25% of the amino acid resdues are DOPA. A few examples of typical peptide units are given below. However, it is important to note that the amino acid sequences of these proteins are variable and that the scope of the present invention is not limited to the exemplified subsequences below as the skilled person realises that bioadhesive polyphenolic proteins from different sources can be regarded as equivalent:

a) Val-Gly-Gly-DOPA-Gly-DOPA-Gly-Ala-Lys
b) Ala-Lys-Pro-Ser-Tyr-diHyp-Hyp-Thr-DOPA-Lys
c) Thr-Gly-DOPA-Gly-Pro-Gly-DOPA-Lys
d) Ala-Gly-DOPA-Gly-Gly-Leu-Lys
e) Gly-Pro-DOPA-Val-Pro-Asp-Gly-Pro-Tyr-Asp-Lys
f) Gly-Lys-Pro-Ser-Pro-DOPA-Asp-Pro-Gly-DOPA-Lys
g) Gly-DOPA-Lys
h) Thr-Gly-DOPA-Ser-Ala-Gly-DOPA-Lys
i) Gln-Thr-Gly-DOPA-Val-Pro-Gly-DOPA-Lys
j) Gln-Thr-Gly-DOPA-Asp-Pro-Gly-Tyr-Lys
k) Gln-Thr-Gly-DOPA-Leu-Pro-Gly-DOPA-Lys

As disclosed herein, the term "polymer comprising carbohydrate groups", relates to a naturally occurring or synthetic polymer comprising a plurality of carbohydrate groups. The polymers can be constituted of discrete carbohydrate groups joined by hydrocarbon chains, but preferably the polymers are polysaccharides, and still more preferably polysaccharides comprising charged groups. Examples of suitable polymers are heparin, chondroitin sulfate, chitosan and hyaluronan.

As disclosed herein, the term "pharmaceutically acceptable fine filaments" relates to thin fibres which can be used in sutures, preferably ophthalmic sutures. For the purposes of the present invention, the lengths of the fibres should not exceed 15 mm, and are typically within the range of 1–10 mm.

As disclosed herein, the term "filler protein" relates to a protein that is optionally added to the bioadhesive composition in order to obtain a bioadhesive composition that is adapted to special applications. Suitable filler proteins according to the present invention are collagen, casein, albumin, elastin, fibrin and fibronectin.

By the term "enzymatic oxidising agent" is meant an enzyme having the ability of oxidising MAP in order to promote full or partial cross-linking of MAP and/or polymers and/or filler proteins. Examples of such enzymes according to the state of the art include catechol oxidase and tyrosinase. A composition according to the present invention does not include an enzymatic oxidising agent. By the term "non-enzymatic oxidising agent" is meant a pharmaceutically acceptable oxidising agent which, at the doses employed, is non-toxic and non-irritating. Examples of such non-enzymatic oxidising agents are hydrogen peroxide and sodium nitroprusside.

By the term "chemical cross-linking agent" is meant a compound comprising at least two functional groups that are able to covalently couple to MAP and/or polymers and/or filler proteins. Examples of such compounds according to the state of the art include glutaraldehyde, formaldehyde, bis(sulfosuccinimidyl) suberate and 3,3'-dithiobis (sulfosuccinimidyl propionate). A composition according to the present invention does not include any chemical cross-linking agent.

A composition according to the present invention comprises two mandatory components, namely a) a bioadhesive polyphenolic protein, and b) a polymer comprising carbohydrate groups. It is preferred that the composition is supplied as a kit of parts, wherein the above mentioned mandatory components are comprised in separate preparations. These preparations are mixed immediately before use. In the complete composition, the following concentrations have been found to be useful:

| Component | Concentration (mg/ml) |
| --- | --- |
| polyphenolic protein (component a) | 0.1–50, preferably 0.3–10 |
| polymer with carbohydrate groups | 0.1–50, preferably 0.3–30 |

Optionally, a non-enzymatic oxidising agent can be included. One such agent is hydrogen peroxide, which typically can be included in an amount of 1–100 mg/ml, preferably about 10 mg/ml corresponding to 1% (w/v). Other such agents are nitroprusside ions and periodate ions. Periodates, such as sodium periodate, are typically in a concentration of 2 mM counted on the final composition. Furthermore, pharmaceutically acceptable fine filaments can be included in an amount of 0.5–40 mg/ml, preferably 1–20 mg/ml of the final composition.

In case the composition is supplied as a kit of parts, each component is provided in the same or a higher concentration, but the above mentioned concentration ranges will be obtained upon mixing the component preparations with each other in order to prepare the final composition.

The present invention will now be further described in the following non-limiting examples.

EXAMPLE 1

Extensively purified mussel adhesive protein (MAP) was used, supplied by BioPolymer Products AB, Floda, Sweden, in 5% acetic acid at a concentration of 0.9 mg/mL, and stored in the darkness in the cold (~8° C.). Heparin from swine intestinal mucosa was purchased from Sigma Chemical Co., St. Louise, Mo., USA (H 3393). Additional laboratory chemicals were of highest available purity and purchased from Sigma and Merck.

The pH of the MAP solution was adjusted to a slightly alkaline pH, usually to 7,5–8.5 but in additional experiments up to about 9.5. The experiments were performed on anaesthetised rats.

The cornea was deepithelialized. A wound was created surgically in the centre of the cornea, with the aid of a trephine with diameter of 3 mm. The Bowmans membrane and stroma was excised with a knife and fine scissors, down to the vicinity of Descemets membrane. A block of corneal tissue was thereby isolated and removed from its original site. At least 5 µL of MAP and 3 µL 10 mg/ml aqueous heparin solution was administrated into the wound cavity and thereafter were the shortly before removed corneal tissue pieces repositioned into the cavity to test for adhesion and reattachment mediated by the MAP glue. Adherents was achieved between the stroma fragments and the wound cavity in the cornea after 5 minutes, as very gently tested with the aid of ophthalmic tweezers and an operating microscope. The MAP-glue combination did not add any obvious extra intensity with regard to the inflammatory reactions during the first days. The corneal wound was covered by epithelium within two days. No adverse effects could be recognised by visual inspection or by microscopy that could be related to the MAP composition.

Histopathological examinations of those corneae, that still had stromal fragments attached, after 5 and 7 days revealed that the MAP-heparin combination seemingly did not aggravate the inflammatory response in either the cornea or in the limbus and conjunctiva as compared to that in specimens from animals having had a wound cavity in the cornea for the same time period. There was in places down-growth of epithelial cells into the corneal wound beneath the reattached stromal fragments, but not to that extend that they detached.

EXAMPLE 2

Purified MAP (0.81 mg/mL, BioPolymer Products AB) in either 1% citric or 1% lactic acid had its pH adjusted to usually to 7,5–8.5, but in some experiments up to about 9.5. Heparin and laboratory chemicals were of highest available purity and purchased from Sigma and Merck. The experiments were performed on anaesthetised rats according to the rules specified by the ethical permissions.

The cornea was deepithelialized. A wound was created surgically in the centre through roughly half of the cornea, with the aid of a trephine with diameter of 3 mm. The Bowmans membrane and stroma was excised with a knife and fine scissors, down to the vicinity of Descemets membrane. A block of corneal tissue was thereby isolated and removed from its original site. At least 5 µL of MAP, 3 µL 10 mg/ml aqueous heparin solution and 2 µL 6% (w/v) aqueous hydrogen peroxide was administrated into the wound cavity, either once or twice. Thereafter was the shortly before removed corneal tissue pieces repositioned into the cavity to test for adhesion and reattachment mediated by the MAP glue. Bonding was achieved between the stroma fragments and the wound cavity in the cornea after 5 minutes, as very gently tested with the aid of ophthalmic tweezers and an operating microscope. The MAP-glue combination did not add any obvious extra intensity with regard to the inflammatory reactions during the first days. The corneal wound was covered by epithelium within two days. No adverse effects could be recognised by visual inspection or by microscopy that could be related to the MAP composition.

Histopathological examinations of corneae with stromal fragments attached, after 5 and 7 days revealed that the MAP-heparin combination seemingly did not aggravate the inflammatory response in either the cornea or in the limbus and conjunctiva as compared to that in specimens from animals having had a wound cavity in the cornea for the same time period. There was in places down-growth of epithelial cells into the corneal wound beneath the reattached stromal fragments, but not to that extend that they detached due to loss of contact with the corneal stroma.

EXAMPLE 3

Purified MAP (0.81 mg/mL, BioPolymer Products AB) in either 1% citric or 1% lactic acid had its pH adjusted to usually to 7,5–8.5, in some experiments up to about 9.5. Chondroitin sulfate and laboratory chemicals were of highest available purity and purchased from Sigma and Merck. The experiments were performed on anaesthetised rats according to the rules specified by the ethical permissions.

The cornea was deepithelialized. A wound was created surgically in the centre through roughly half of the cornea, with the aid of a trephine with diameter of 3 mm. The Bowmans membrane and stroma was excised with a knife and fine scissors, down to the vicinity of Descemets membrane. A block of corneal tissue was thereby isolated and removed from its original site. At least 5 µL of MAP, 3 µL 24 mg/ml aqueous chondroitin sulphate and 2 µL 6% (w/v) aqueous hydrogen peroxide was administrated into the wound cavity, either once or twice. Thereafter was the shortly before removed corneal tissue pieces repositioned into the cavity to test for adhesion and reattachment mediated by the MAP glue. Bonding was achieved between the stroma fragments and the wound cavity in the cornea after 5 minutes, as very gently tested with the aid of ophthalmic tweezers and an operating microscope. The MAP-glue combination did not add any obvious extra intensity with regard to the inflammatory reactions during the first days. The corneal wound was covered by epithelium within two days, although there seemed to be irregularities in the epithelial cell layering. No adverse effects could be recognised by visual inspection or by microscopy that could be related to the MAP composition.

Histopathological examinations of corneae with stromal fragments attached, after 5 and, for one rat, 7 days revealed that the MAP-chondroitin sulphate combination seemingly did not aggravate the inflammatory response in either the cornea or in the limbus and conjunctiva as compared to that in specimens from animals having had a wound cavity in the cornea for the same time period. There was no distinct down-growth of epithelial cells into the corneal wound.

EXAMPLE 4

Purified MAP (0.81 mg/mL, BioPolymer Products AB) in either 1% citric or 1% lactic acid had its pH adjusted to usually to 7,5–8.5, in some experiments up to about 9.5. Hyaluronan (aqueous solution, 10 mg/ml), chitosan (aqueous solution, 10 mg/ml) and laboratory chemicals were of highest available purity. The experiments were performed on anaesthetised rats according to the rules specified by the ethical permissions.

The surgical procedure was performed as in exampel 1–3. Fairly good bonding were achieved between the stromal pieces and the surrounding orignal cornea. The achieved results were in agreement with those reported in Example 1–3. However, histopthalogical examination revealed that was some down-groth of peithelial cells along the lateral borders of the implanted stroma, but to a limited extent.

EXAMPLE 5

Purified MAP (0.81 mg/mL, BioPolymer Products AB) in 1% lactic acid had its pH adjusted to usually to 7,5–8.5, in additional experiments occasionally up to about 9.5. Heparin and laboratory chemicals were of highest available purity and purchased from Sigma and Merck. The experiments were performed on anaesthetised rats according to the rules specified by the ethical permissions.

The cornea was deepithelialized. The cornea was carefully punched in the centre with the aid of a trephine with diameter of 3 mm. The tissue cylinder was slowly retracted to at least half of its thickness from the original cornea with the aid of fine-pointed instruments under microscopic observation. A solution, prepared immediately before use, of 20 µL MAP, 10 µL 10 mg/ml aqueous solution of heparin and 10 µL 6% (w/v) aqueous hydrogen peroxide was applied along the border between the plug and the remaining cornea. The cornea plug was then repositioned and gently kept in position. Adhesion was achieved between the central plug and peripheral part of the original cornea after 5 minutes, as very gently tested with the aid of ophthalmic tweezers and an operating microscope.

Visual inspection and microscopy was performed during 5 days, and occasionally 7 days. There was an inflammatory reaction in the conjunctiva and blood vessels tended to grow towards the area of surgery. The central cornea remained in position fixed to the surrounding cornea. The cornea was re-epethilialized in 2 days. There was edema and slight to moderate opacities in and adjacent to the wound area. Histopathology of the cornea revealed a slight to moderate inflammation along the zone of surgery. Epithelial cells cover the anterior surface but as well could be detected as strings along parts the lateral interface of the corneal plug. Leukocytes and macrophages adhered to the zone of injury, facing the anterior chamber. The achieved results thus indicate that MAP in conjunction with heparin and an oxidising agent could be used to safely glue a corneal plug back to its site of surgery.

EXAMPLE 6

Purified MAP (0.81 mg/mL, BioPolymer Products AB) in 1% citric acid had its pH adjusted to usually to 7,5–9.5. Heparin and laboratory chemicals were of highest available purity and purchased from Sigma and Merck. The experiments were performed on anaesthetised rats according to the rules specified by the ethical permissions.

The cornea was deepithelialized. Surgery and application of the bonding mixture was performed as in example 5. Adhesion was achieved between the central plug and peripheral part of the original cornea after 5 minutes, as very gently tested with the aid of ophthalmic tweezers and an operating microscope.

The results obtained was in good agreement with those presented in example 5 for in this case MAP in citric acid and heparin, both with regard to the clinical outcome and the histopatholoy as investigated after 5 days.

EXAMPLE 7

Purified MAP (0.81 mg/mL, BioPolymer Products AB) in 1% citric acid had its pH adjusted to usually to 7,5–8.5. Chondroitin sulphate (24 mg/ml aqueous solution) and laboratory chemicals were of highest available purity and purchased from Sigma and Merck. The experiments were performed on anaesthetised rats according to the rules specified by the ethical permissions.

The cornea was deepithelialized. Surgery and application of the bonding mixture was performed as in example 5. Adhesion was achieved between the central plug and peripheral part of the original cornea after 5 minutes, as very gently tested with the aid of ophthalmic tweezers and an operating microscope.

Visual inspection and microscopy was performed during 5 days, and occasionally 7 days. There was an inflammatory reaction in the conjunctiva and blood vessels tended to grow towards the area of surgery. The central cornea autograft remained in position fixed to the surrounding cornea. The cornea was re-epethilialized in 2 days. There was edema and slight to moderate opacities in and adjacent to the wound area. Histopathology of the cornea revealed a slight to moderate inflammation in the zone of surgery. Epithelial cells cover the anterior surface. However, along the lateral interface of the plug and the cornea only short, but seemingly wide papilla of epithelial cells could be recognised. In none of the sections examined reached the epithelium more than about one fourth or one third of the depth of the corneal stroma. Leukocytes and macrophages adhered to the zone of injury, facing the anterior chamber. The achieved results thus indicate that MAP (in citric acid) in conjunction with chondroitin sulphate and an oxidising agent could be used to safely secure a corneal tissue plug to its site of surgery.

EXAMPLE 8

Purified MAP (0.81 mg/mL, BioPolymer Products AB) in 1% lactic acid had its pH adjusted to 7,5–9.5. Chondroitin sulphate (24 mg/ml, aqeous solution) and laboratory chemicals were of highest available purity and purchased from Sigma and Merck. The experiments were performed on anaesthetised rats according to the rules specified by the ethical permissions.

The cornea was deepithelialized. The surgery and the treatment with MAP, chondroitin sulphate and oxidizing agent was performed as in example 7.

The results obtained agreed with those in example 7 The achieved results thus indicate that MAP (in lactic acid) in conjunction with chondroitin sulphate and an oxidising agent could be used to safely reattach a corneal tissue plug to the cornea.

EXAMPLE 9

Purified MAP (0.81 mg/mL, BioPolymer Products AB) in either 1% lactic acid or in 1% citric acid had its pH adjusted to 7,5–9.5. Chitosan (10 mg/ml, aqeous solution), hyaluronan (10 mg/ml, aqeous solution) and laboratory chemicals were purchased to be of highest available purity. The experiments were performed on anaesthetised rats according to the rules specified by the ethical permissions.

The cornea was deepithelialized. The surgery and the treatment with MAP, hyaluronan or chitosan and oxidizing agent was performed as in example 7. The results obtained with chitosan roughly agreed with those in example 7, while hyaluronan worked in the acute situation but no long term results were achieved. The results indicate that MAP in conjunction with additional polysaccharides and an oxidising agent could be used to reattach a corneal tissue plug to the cornea.

EXAMPLE 10

Purified MAP (0.9 mg/mL, BioPolymer Products AB) in 5% acetic acid had its pH adjusted to become alkaline. Heparin and laboratory chemicals were of highest available purity and purchased from Sigma and Merck. The experiments were performed on anaesthetised rats according to the rules specified by the ethical permissions.

The cornea was deepithelialized. Surgery and application of the bonding mixture was performed as in example 5. Adhesion was achieved between the central plug and peripheral part of the original cornea, as gently tested after 10 minutes with the aid of ophthalmic tweezers and an operating microscope.

The results obtained was in good agreement with those presented in example 5 for in this case MAP in acetic acid and heparin, both with regard to the clinical outcome and the histopatholoy as investigated after 5 days.

EXAMPLE 11

Purified MAP (0.81 mg/ml, BioPolymer Products AB) in 1% lactic acid had its pH adjusted to 7.5–9.5. Heparin and laboratory chemicals were of highest available purity and purchased from Sigma and Merck. Ophthalmic sutures (10-0) were purchased from Ethicon, cut in small pieces ranging in length from 1–10 mm and eventually added to the MAP solution. The experiments were performed on anaesthetised rats according to the rules specified by the ethical permissions.

The cornea was deepithelialised. The cornea was carefully punched in the centre with aid of a trephine with a diameter of 3 mm. The tissue cylinder was slowly reacted to at least half of its thickness from the original cornea with aid of fine-pointed instruments under microscopic observation. Two small marks were made in the periphery of the central cornea plug. A solution, prepared immediately before use, of 20 µl MAP solution, 10 µl aqueous heparin solution, ophthalmic sutures (10 mg/ml of the final composition)and 10 µl 6% (w/v) aqueous hydrogen peroxide solution, was applied several times along the border between the plug and the remaining cornea. The cornea plug was then repositioned and gently kept in position. Adhesion was achieved between the central plug and peripheral part of the original cornea after 5–10 minutes, as very gently tested with aid of ophthalmic microsurgery instruments using an operating microscope.

Visual inspection and microscopy was performed during the subsequent 3 hours. There was good adhesion between the central corneal plug and the surrounding residuing cornea. The small defects in the interface zone were filled by the glue with its filaments.

The achieved results thus indicate that MAP in conjunction with heparin, an oxidising agent and very fine filaments could be used to safely glue a corneal plug back to its site of surgery and to fill and bridge defects in the tissue.

EXAMPLE 12

Purified MAP (0.81 mg/mL, BioPolymer Products AB) in either 1% citric or 1% lactic acid had its pH adjusted to usually to 7,5–8.5, but in some experiments up to about 9.5. Heparin and laboratory chemicals were of highest available purity and purchased from Sigma and Merck. The experiments were performed on anaesthetised rats according to the rules specified by the ethical permissions.

The cornea was deepithelialized. A wound was created surgically in the centre through roughly half of the cornea, with the aid of a trephine with diameter of 3 mm. The Bowmans membrane and stroma was excised with a knife and fine scissors, down to the vicinity of Descemets membrane. A block of corneal tissue was thereby isolated and removed from its original site. At least 5 µL of MAP, 3 µL 10 mg/ml aqueous heparin solution and 2 µL 2 mM sodium periodate was administrated into the wound cavity, either once or twice. Thereafter was the shortly before removed corneal tissue pieces repositioned into the cavity to test for adhesion and reattachment mediated by the MAP glue. Bonding was achieved between the stroma fragments and the wound cavity in the cornea after 5 minutes, as very gently tested with the aid of ophthalmic tweezers and an operating microscope. The MAP-glue combination did not add any obvious extra intensity with regard to the inflammatory reactions during the first days. The corneal wound was covered by epithelium within two days. No adverse effects could be recognised by visual inspection or by microscopy that could be related to the MAP composition.

EXAMPLE 13

Purified MAP (0.81 mg/mL, BioPolymer Products AB) in either 1% citric or 1% lactic acid had its pH adjusted to usually to 7,5–8.5, but in some experiments up to about 9.5. Heparin and laboratory chemicals were of highest available purity and purchased from Sigma and Merck. The experiments were performed on anaesthetised rats according to the rules specified by the ethical permissions.

The cornea was deepithelialized. A wound was created surgically in the centre through roughly half of the cornea, with the aid of a trephine with diameter of 3 mm. The Bowmans membrane and stroma was excised with a knife and fine scissors, down to the vicinity of Descemets membrane. A block of corneal tissue was thereby isolated and removed from its original site. At least 5 µL of MAP, 3 µL 10 mg/ml aqueous heparin solution and 2 µL 2 mM sodium nitroprusside was administrated into the wound cavity, either once or twice. Thereafter was the shortly before removed corneal tissue pieces repositioned into the cavity to test for adhesion and reattachment mediated by the MAP glue. Bonding was achieved between the stroma fragments and the wound cavity in the cornea after 5 minutes, as very gently tested with the aid of ophthalmic tweezers and an operating microscope. The MAP-glue combination did not add any obvious extra intensity with regard to the inflammatory reactions during the first days. The corneal wound was covered by epithelium within two days. No adverse effects could be recognised by visual inspection or by microscopy that could be related to the MAP composition.

What is claimed is:

1. A method of preparing an ophthalmic adhesive, comprising combining a bioadhesive polyphenolic protein and a polymer comprising carbohydrate groups to form an ophthalmic adhesive, wherein said bioadhesive polyphenolic protein is derived from a byssus-forming mussel comprises 30–300 amino acids and consists essentially of tandemly linked peptide repeats comprising 3–15 amino acid residues, wherein at least 5% of the amino acid residues of said bioadhesive polyphenolic protein are L-3,4-dihydroxyphenylalanine;

and wherein enzymatic oxidizing agents or chemical cross-linking agents are not added.

2. The method according to claim 1, wherein said polymer comprising carbohydrate groups are selected from the group consisting of heparin, chondroitin sulfate, chitosan and hyaluronan.

3. The method according to claim 1, further comprising adding pharmaceutically acceptable fine filaments, a non-enzymatic oxidizing agent, and a filler protein to said bioadhesive composition.

4. A method for healing performations, lacerations, or incisions, reattaching a retina to the back of an eye, repairing or attaching lenses, and repairing, constructing, reconstructing and/or attaching corneal component parts, comprising:

applying an effective amount of a composition to said performations, lacerations, or incisions, to reattach the retina to the back of the eye, to repair or attach lenses, and to repair, construct, reconstruct and/or attach corneal components parts, said composition comprising a component a) a bioadhesive polyphenolic protein derived from a byssus-forming mussel, said protein comprises 3–300 amino acids and consists essentially of tandemly linked peptide repeats comprising 3–15 amino acid residues, wherein at least 5% of the amino acid residues of said bioadhesive polyphenolic protein are L-3,4-dihydroxyphenylalanine, and component b) a polymer comprising carbohydrate groups, wherein said components are in the form of a combined bioadhesive preparation for simultaneous medical use, and wherein said combined bioadhesive preparation does not comprise any enzymatic oxidizing agent or chemical cross-linking agent.

5. The method according to claim 4, wherein said composition comprises a polymer comprising carbohydrate groups selected from the group consisting of heparin, chondroitin sulfate, chitosan and hyaluronan.

6. The method according to claim 4, wherein said composition further comprises pharmaceutically fine filaments, non-enzymatic oxidizing agents, and filler proteins to said bioadhesive composition.

* * * * *